United States Patent [19]
Shigeyasu et al.

[11] 3,956,175
[45] May 11, 1976

[54] METHOD FOR RECOVERING A LIQUID-PHASE OXIDATION CATALYST FOR PREPARATION OF TEREPHTHALIC ACID

[75] Inventors: Motoo Shigeyasu, Matsuyama; Hatsutaro Yamazaki, Matsue; Michio Kuki, Matsuyama, all of Japan

[73] Assignee: Matsuyama Petrochemicals Inc., Osaka, Japan

[22] Filed: Apr. 22, 1974

[21] Appl. No.: 463,025

[30] Foreign Application Priority Data
Apr. 20, 1973 Japan .............................. 48-44841

[52] U.S. Cl. .............................. 252/412; 252/416; 260/524 R; 423/50; 423/140; 423/144
[51] Int. Cl.² .................... B01J 37/00; C07C 51/42; C01G 45/00; C01G 51/06
[58] Field of Search .................. 252/416, 413, 412; 260/524 R, 525; 423/42, 140, 144

[56] References Cited
UNITED STATES PATENTS

| | | | |
|---|---|---|---|
| 2,964,559 | 12/1960 | Burney | 260/525 |
| 3,033,899 | 5/1962 | Knobloch et al. | 260/525 |
| 3,105,851 | 10/1963 | Knobloch et al. | 260/525 |
| 3,341,470 | 9/1967 | Hensley, Jr. | 252/413 |
| 3,673,154 | 6/1972 | Trevillyah | 260/524 R |
| 3,840,641 | 10/1974 | Wampfler et al. | 260/525 |

*Primary Examiner*—Winston A. Douglas
*Assistant Examiner*—P. E. Konopka
*Attorney, Agent, or Firm*—Sughrue, Rothwell, Mion, Zinn & Macpeak

[57] ABSTRACT

A method for recovering a heavy metal oxidation catalyst used in a liquid-phase oxidation process for producing terephthalic acid from the residue of the reaction mother liquor by stirring the residue together with water in the presence of molecular oxygen and a sulfur compound, subjecting the extracted mixture to a solid-liquid separation to separate the solid impurities, adding the aqueous solution containing the oxidation catalyst to an alkali metal or ammonium carbonate or an aqueous solution of an alkali metal or ammonium carbonate while maintaining the temperature of the system at about 26°C to 70°C, and recovering the heavy metal catalyst as a carbonate precipitate having high purity and good filterability and washability.

21 Claims, 3 Drawing Figures

METHOD FOR RECOVERING A LIQUID-PHASE OXIDATION CATALYST FOR PREPARATION OF TEREPHTHALIC ACID

BACKGROUND OF THE INVENTION

1. Field of the Invention

This invention relates to a method for recovering an oxidation catalyst used for the preparation of terephthalic acid by the liquid-phase oxidation of an alkylbenzene such as para-xylene with a gas containing molecular oxygen from the residue of the reaction mother liquor, and more specifically, to a method for recovering a heavy metal catalyst such as manganese or cobalt as a carbonate precipitate having purity and good filterability.

2. Description of the Prior Art

Commercial methods for preparing terephthalic acid which are now widely accepted involve the liquid-phase oxidation of alkylbenzenes such as para-xylene with a gas containing molecular oxygen in a lower aliphatic monocarboxylic acid as a solvent in the presence of a catalyst containing a heavy metal such as cobalt, manganese, or a bromine compound. Terephthalic acid is separated from the reaction mixture resulting from such a liquid-phase oxidation reaction by means such as filtration or centrifugal separation, and then the reaction solvent is recovered from the reaction mother liquor by means such as distillation. The residue resulting after the removal of the solvent contains the heavy metal catalyst. In order to utilize expensive metals such as cobalt and manganese effectively, it is important to reuse the heavy metal catalyst. In addition to the heavy metal catalyst, however, the residue of the mother liquor contains great quantities of unreacted alkylbenzene, and organic impurities such as 4-carboxybenzaldehyde and para-toluic acid as reaction intermediates and unidentified oxidation by-products.

Furthermore, since acetic acid, for example, is used as the solvent under high temperature and pressure conditions, and a halogen such as bromine is also used as a catalyst component in the above liquid-phase oxidation reaction, the reaction liquor is corrosive. While such a reaction liquor circulates within the system, corrosion of the equipment takes place, and metals such as iron, chromium, nickel, molybdenum or copper contained in the materials of the equipment contaminate the reaction liquor. In addition, the terephthalic acid which is sparingly soluble in the solvent deposits on various parts of the manufacturing equipment and on the inside walls of the pipes and causes blockage. In order to prevent such blockage, the equipment is washed with an aqueous solution of an alkali such as sodium hydroxide, and this often results in the contamination of the reaction liquor with the alkali metal. It is known that all of these impurities impede the oxidation reaction of alkylbenzenes and cause a reduction in the quality and yield of terephthalic acid. Accordingly, when the oxidation reaction catalyst is recovered from the residue of the mother liquor for recycling, it is important to prevent impurities such as the organic impurities, the heavy metal impurities and the alkali metal from contaminating the heavy metal catalyst recovered. Various methods have therefore been proposed to recover the oxidation catalyst without contamination by various impurities.

For example, U.S. Pat. No. 2,964,559 discloses a method which comprises extracting the residue of the mother liquor containing tar-like by-products with a solvent such as water, a lower aliphatic carboxylic acid or a mixture thereof to thereby recover a heavy metal catalyst such as cobalt or manganese as an extract not containing the tar-like by-products. U.S. Pat. No. 3,341,470 discloses a method of recovering the heavy metal catalyst without contamination with tar-like organic by-products and metal impurities such as iron, chromium or copper contained in the residue of the reaction mother liquor. Specifically, the method comprises incinerating the residue of the reaction mother liquor to thereby oxidize the heavy metal catalyst, dissolving the catalyst in a mineral acid such as sulfuric acid, adding sodium sulfide or hydrogen sulfide, etc. to the solution to remove any copper contaminant in the form of a copper sulfide precipitate, then diluting the solution with water, neutralizing the diluted solution with a hydroxide to a pH of about 4, adding calcium carbonate to the solution to separate metal impurities such as iron or chromium as their oxide precipitates, adding sodium carbonate to the solution from which the metal impurities have been removed, to thereby obtain cobalt or manganese as a carbonate precipitate, and finally treating the precipitate with an organic carboxylic acid to recover cobalt or manganese as the organic carboxylate.

Furthermore, Japanese Patent Publication 14339/71 discloses a method comprising: extracting the residue of the reaction mother liquor containing oxidation reaction by-products and iron with water as an extracting solvent to separate the insoluble solid impurities, adding an alkali to the aqueous solution containing the extracted oxidation catalyst to adjust the pH of the aqueous solution to 4 to 5 and separating the tar-like by-products as a float and the iron as a basic iron acetate precipitate, and thereafter adding an alkali metal such as sodium carbonate to recover the cobalt or manganese as a carbonate precipitate carbonate.

Japanese Laid-Open Patent Publication 34088/72 discloses a method comprising: extracting the residue of the reaction mother liquor with water to separate insoluble solid impurities, adding an alkali to the aqueous extract to adjust the pH of the aqueous extract to 6.0 to 6.8, either separating iron and lead as a sparingly soluble terephthalate or oxidizing the iron compound in the aqueous extract to a trivalent iron compound and thereafter adjusting the pH of the aqueous extract to 4.0 to 6.8 to separate iron or lead as a sparingly soluble terephthalate, and adding a carbonate compound such as sodium carbonate to the resulting filtrate to recover cobalt or manganese as the carbonate.

The procedure of adding an alkali metal or carbonate to the aqueous extract obtained by extracting the residue of the mother liquor containing the heavy metal catalyst with water thereby to recover the heavy metal catalyst as a carbonate precipitate, which is employed in many of the prior techniques illustrated above, is considered to be a superior method capable of recovering the heavy metal catalyst in a highly pure form without contamination with impurities detrimental to the oxidation reaction.

However, according to this procedure, the precipitated particles of the heavy metal carbonate such as cobalt carbonate or manganese carbonate are recovered as very fine amorphous colloidal particles. Accordingly, long periods of time are required to separate the precipitate of the heavy metal carbonate from the precipitate-containing solution and to wash the separated precipitate with water. Thus, for commercial operation, this separating apparatus requires enormous filtering and washing areas. The formation of precipitated particles which can be easily filtered and washed has been regarded as an industrially important problem.

One measure for coping with this problem is disclosed, for example, in Japanese Laid-Open Patent Publication 1553/72 which discloses a method wherein an alkali metal carbonate is added to the heavy metal(-cobalt)-containing solution extracted from the residue of the mother reaction liquor with water at a temperature of not less than 170°F (77°C), preferably at least 195°F (91°C), to thereby precipitate the cobalt as a carbonate having improved filterability and washability. However, the precipitated particles obtained by this method are still unsatisfactory from the standpoint of filterability and washability. Furthermore, since the precipitation of the carbonate in this method is performed at an elevated temperature, the alkali metal carbonate abruptly decomposes, evolving carbon dioxide which forms bubbles insoluble in the solution. This not only leads to the loss of the alkali metal carbonate, but also results in a marked expansion of the volume of the solution, which in turn requires a tank of increased capacity for forming the precipitate.

As stated above, no advantageous method has yet been discovered for recovering a heavy metal catalyst such as cobalt or manganese used in the liquid-phase oxidation of alkylbenzenes to produce terephthalic acid from the mother liquor residue as a carbonate precipitate having good filterability and washability while efficiently removing the organic impurities or heavy metal impurities such as chromium, iron, nickel or copper, all of which are detrimental to the oxidation reaction.

SUMMARY OF THE INVENTION

Investigations have been made to establish an advantageous method for recovering a heavy metal catalyst such as cobalt or manganese as a carbonate precipitate having good filterability and washability in a highly pure form which is free from organic impurities or heavy metal impurities. As a result, it has now been discovered that heavy metal catalysts such as cobalt and manganese can be recovered as a highly pure crystalline heavy metal carbonate precipitate having good filterability and washability from the reaction mother liquor residue of the liquid-phase oxidation, by stirring the residue with water in the presence of an oxygen-containing gas and a sulfur compound to form an aqueous extract of the catalyst free from the organic impurities and heavy metal impurities, and adding the aqueous extract of the catalyst to an alkali metal or ammonium carbonate or an aqueous solution of an alkali metal or ammonium carbonate at a temperature ranging from room temperature to a slightly elevated temperature to thereby obtain a crystalline heavy metal carbonate precipitate.

Accordingly, it is an object of this invention to provide a method for recovering a heavy metal catalyst such as cobalt or manganese as a carbonate having good filterability and washability in a highly pure form free from which is organic impurities and heavy metal impurities such as iron, chromium or copper from a residue of the reaction mother liquor obtained in the recovery of terephthalic acid and the solvent from the oxidation reaction product which is obtained by the liquid-phase oxidation reaction of an alkylbenzene, such as para-xylene, to produce terephthalic acid.

Another object of this invention is to provide an improved method for recovering the heavy metal catalyst as a carbonate precipitate having good filterability and washability by extracting the heavy metal catalyst from the residue of the reaction mother liquor using water as a solvent, and mixing the resulting aqueous solution containing the extracted heavy metal catalyst with an alkali metal or ammonium carbonate.

Still another object of this invention is to provide a method wherein the residue of the reaction mother liquor is extracted with water, the resulting aqueous solution containing the extracted heavy metal catalyst is mixed with an alkali metal or ammonium carbonate, and the resulting precipitate of the heavy metal catalyst carbonate is recovered in a highly pure form from the precipitate-containing solution without adsorption of impurities such as an alkali metal on the precipitate.

These and other objects of this invention will become more apparent from the following detailed description of the invention and the accompanying drawings.

DETAILED DESCRIPTION OF THE INVENTION

The present invention provides a method for recovering a heavy metal oxidation catalyst from the residue of the reaction mother liquor containing the oxidation catalyst, organic impurities and a small amount of heavy metal impurities, the residue being obtained by removing the reaction medium from the reaction mother liquor remaining after recovering terephthalic acid from the oxidation reaction product obtained in the process for producing terephthalic acid by subjecting an alkylbenzene such as para-xylene to a liquid-phase oxidation with oxygen or an oxygen-containing gas in the presence of a heavy metal containing catalyst using a lower aliphatic monocarboxylic acid as a solvent, which method comprises:

A. stirring the residue in the presence of a sulfur compound using water as a solvent while blowing a gas containing molecular oxygen into the solution or introducing a gas containing molecular oxygen under pressure, to thereby extract the oxidation catalyst with water, B. subjecting the extracted mixture to a solid-liquid separation to separate the solid organic impurities and heavy metal impurities, C. adding the resulting aqueous solution containing the extracted oxidation catalyst to an alkali metal or ammonium carbonate or an aqueous solution of an alkali metal or ammonium carbonate while maintaining the temperature of the system at 26°C to 70°C to form a precipitate of a carbonate of the heavy metal catalyst, and D. subjecting the precipitate-containing solution to a solid-liquid separation to recover the heavy metal catalyst as a carbonate precipitate.

According to the method of this invention, the residue of the reaction mother liquor is extracted with water as an extracting solvent, and therefore, most of the organic impurities present in large quantities in the residue which are sparsely soluble in water are separated as precipitates or floats from the liquid phase extracted. A part of the organic impurities remaining dissolved in small amounts in the extract is oxidized or polymerized with the molecular oxygen-containing gas blown in the extracting step, and separated from the extract as precipitates or floats. Furthermore, the heavy metal impurities such as iron or chromium dissolved in the extract are oxidized with the blown molecular oxygen-containing gas and are separated as oxide precipitates. Other heavy metal impurities such as lead, molybdenum, tungsten, copper, nickel or cadmium react with the sulfur compound added in the extracting step and are separated as sulfide precipitates. Thus, by removing the precipitates and the floats liberated from the extraction liquid phase using a solid-liquid separating procedure, a heavy metal catalyst-containing extract free from heavy metal impurities and most of the organic impurities can be obtained.

The extracting step for separating the organic impurities and the heavy metal impurities in accordance with the method of this invention has the following advantages over the conventional methods disclosed in the Japanese Patent Publication 14339/71 and Japanese Laid-Open Patent Publication 34088/72, for example, described above.

In the conventional methods, the extract resulting from the extraction of the residue of the reaction mother liquor with water must be adjusted to a specific pH range by the addition of an alkali in order to remove heavy metal impurities such as iron present in the extract. However, according to the method of the present invention, the complicated and uneconomical step of adjusting the pH of the treating solution can be obviated in the extraction step since the heavy metal impurities are precipitated and removed by the oxygen gas and the sulfur compound. Furthermore, in the conventional methods as described above, the pH of the extract must be increased to a certain value by adding an alkali at the time of separating the heavy metal impurities, but an increase in the pH of the extract results in an increase in the solubility of the organic impurities in the extract. Thus, in the conventional methods, insoluble organic impurities should first be separated using a solid-liquid separating procedure from the extract of the residue of the mother liquor prior to the pH adjustment of the extract in order to prevent the organic impurities from being dissolved in great quantities in the extract. However, according to the method of this invention, it is not necessary to adjust the pH of the extract in the step of separating the heavy metal impurities as precipitates, and therefore, the undesirable phenomenon of the increase in the amount of the organic impurities dissolved as a result of an increase in the pH of the extract does not occur. For this reason, the step of removing the water-insoluble organic impurities prior to removing the heavy metal impurities from the extract of the residue of the mother liquor is not required in the present invention, and both the organic impurities and the heavy metal impurities can be removed simultaneously in one step. (The pH of the residue is usually about 2.5 to 3.5, although it is somewhat affected by the amount of alkali remaining in the reaction unit for preparing terephthalic acid. In the oxidation reaction unit, washing with an aqueous solution of sodium hydroxide, for example, is performed in order to remove the terephthalic acid crystals adhering to the oxidation reaction unit surfaces or to the filtering surface of a centrifugal separator for recovering the terephthalic acid from the reaction product, or to prevent the blockage of slurry-transporting pipes, and the alkali often remains.)

The heavy metal catalyst-containing extract obtained by treating the residue of the mother liquor with water in the presence of a molecular oxygen-containing gas and a sulfur compound to separate the organic impurities and the heavy metal impurities is then subjected to the step of completely removing the organic impurities dissolved in very small amounts in the extract and recovering the heavy metal catalyst as a highly pure carbonate precipitate.

The heavy metal catalyst-containing extract is an acidic aqueous solution, and in order to form a precipitate of a carbonate of the heavy metal catalyst dissolved in this solution, a precipitating agent such as an alkali metal or ammonium carbonate should be added to the solution to adjust the pH of the solution to at least about 7. In order to form a precipitate of crystalline particles having a large particle size which have good filterability and washability, those skilled in the art have considered it preferable to employ a procedure in which a precipitant is added to an acidic solution and gradually the alkalinity of the solution is increased wherein precipitation occurs (see, for example, *HANDBOOK OF INORGANIC CHEMISTRY*, page 514, a Japanese language publication, Aug. 8, 1965, published by Gihodo, ToKyo), specifically to increase the pH of the acidic aqueous solution containing the extracted catalyst to a predetermined value while adding an alkali metal or ammonium carbonate, thereby to form a precipitate of the heavy metal carbonate. However, according to the procedure of the present invention of adding the acidic heavy metal catalyst-containing extract to an alkali metal or ammonium carbonate or an alkali metal or ammonium carbonate aqueous solution (which is contrary to the conventional method just described), the unexpected result of the formation of a precipitate of crystalline heavy metal carbonate having better filterability and washability and larger particle sizes than in the conventional methods can be obtained.

It has further been found that the shape of the precipitate of the heavy metal carbonate is affected by the treating temperature for forming the precipitate. Thus, it has been found that it is not necessary to heat the extract at a high temperature as required in Japanese Laid-Open Patent Publication 1553/72 previously cited, but by forming the precipitate at a temperature of 26°C to 70°C, the precipitate obtained has superior filterability. Accordingly, since the formation of the precipitate is carried out at a relatively low temperature, evolution of carbon dioxide does not occur and there is no loss of the alkali metal or ammonium carbonate. Furthermore, no foaming occurs, and therefore it is not necessary to increase the capacity of the precipitate-forming tank.

The operation of forming a precipitate of the carbonate of the heavy metal catalyst from an aqueous solution containing the extracted catalyst was accomplished on the basis of the above new finding. By the expedient of adding the extract to a precipitant (contrary to the conventional methods) and maintaining the treating temperature within a specific range from room temperature to a slightly elevated temperature, the heavy metal catalyst can be recovered as a precipitate of crystalline particles having a large particle diameter and having superior filterability and washability.

By the recovering method of this invention described above, the heavy metal catalyst such as cobalt or manganese is recovered as a carbonate precipitate substantially free from noxious impurities and having good filterability and washability. At the time when the precipitate of the carbonate of cobalt or manganese, etc. is formed, impurities are not adsorbed on the precipitate. However, when the heavy metal carbonate precipitate is allowed to stand in the alkali metal or ammonium carbonate solution, impurities such as the alkali metal contained in the alkali metal or ammonium carbonate solution are gradually adsorbed on the rate This phenomenon, called a post-precipitation phenomenon, causes a decrease in the precipitate of the precipitate. Especially, the adsorption of alkali metal affects the oxidation reaction, and should therefore be avoided as much as possible. In order, therefore, to obtain the recovered catalyst in the desired purity, it is desirable to separate and recover the precipitate from the alkali metal or ammonium carbonate solution immediately after the formation of the precipitate. However, it is sometimes necessary to let the precipitate-containing solution stand as it is for prolonged periods of time in order to form the precipitate completely and increase the ate of recovery, and in commercial operations, an early separation of the precipiate from the precipitate-containing solution is often difficult. Therefore, prevention of the possibility of adsorption of impurities on the resulting precipitate by, for example, the post-precipitation phenomenon has been studied and it was found that by diluting the precipitate-containing solution with a suitable amount of freshly supplied water after the formation of the precipitate, the adsorption of the impurities can be inhibited even when the precipitate is allowed to stand in the solution for a long time, and the precipitate in the highly pure form can be recovered from the diluted solution by, for example, filtration. Accordingly, by the method of this invention wherein the carbonate precipitate-containing solution is diluted with water prior to solid-liquid separation of the precipitate from the solution, noxious impurities such as alkali metals are not adsorbed on the precipitate of the carbonate of the heavy metal catalyst formed in the alkali metal or ammonium carbonate solution even when the precipitate is allowed to stand in the solution for prolonged periods of time until separation from the solution. Thus, the precipitate can be recovered as a highly pure precipitate, and this is very advantageous in commercial operations.

The residue of the mother liquor to which the method of this invention is applied is a tar-like or solid residue which is obtained by separating and recovering terephthalic acid from an oxidation reaction mixture resulting from the liquid-phase oxidation of an alkylbenzene such as para-xylene with a gas containing molecular oxygen in a lower aliphatic monocarboxylic acid such as acetic acid as a solvent in the presence of a catalyst comprising a heavy metal such as cobalt or manganese or further a halogen such as bromine in addition to the heavy metal, and then removing the reaction solvent from the resulting mother liquor by, for example, distillation. Therefore, any residues of the reaction mother liquor obtained by a method for preparing terephthalic acid by the liquid-phase oxidation of alkylbenzenes using such a heavy metal catalyst or a heavy metal-halogen catalyst, and an initiator such as an aldehyde or ketone can be used in the present invention irrespective of the reaction conditions for obtaining terephthalic acid or the oxidation reaction mode. The residue so obtained contains the unreacted alkylbenzenes, organic impurities such as reaction intermediates (e.g., 4-carboxybenzaldehyde or para-toluic acid) or unidentified by-products, and very small amounts of heavy metal impurities such as iron, chromium, molybdenum, tungsten, lead, nickel and copper resulting from the corrosion of the materials of the reaction apparatus, in addition to the heavy metal catalyst and possibly the halogen. By treating the residue by the method of this invention, the heavy metal catalyst can be recovered as a highly pure carbonate free from noxious impurities and having good filterability and washability at a recovery rate of at least about 95%.

Figure 1:
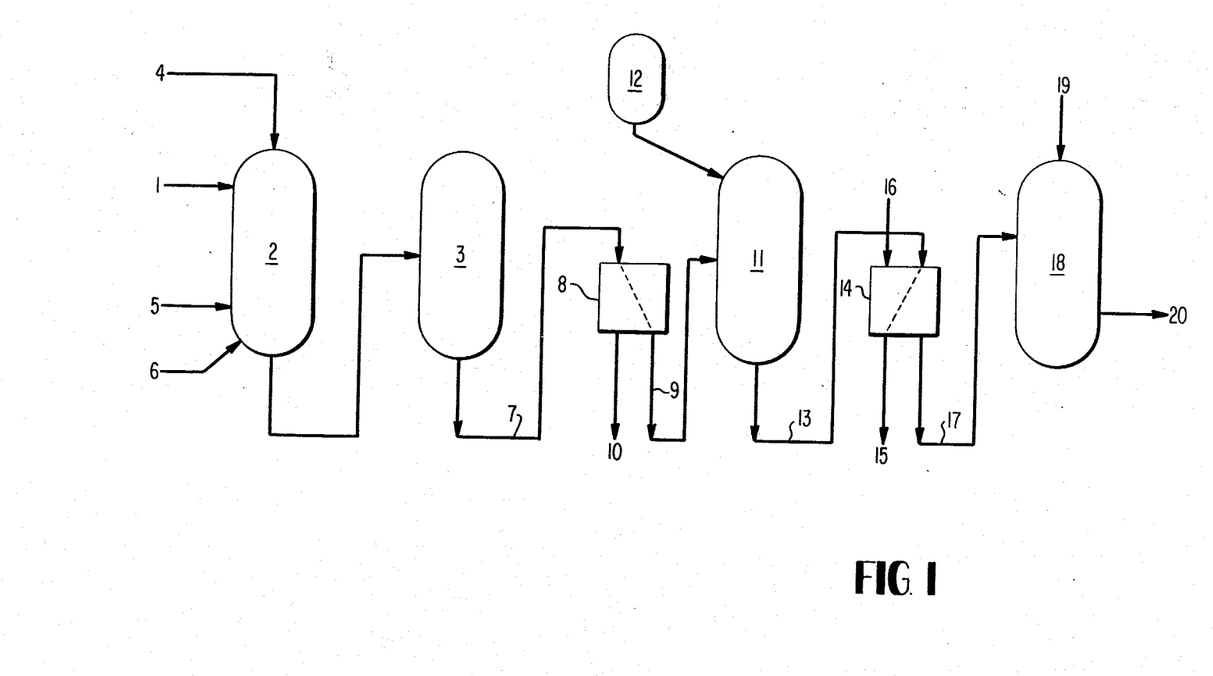
FIG. 1 is a flowsheet illustrating one embodiment of the method of this invention.

One embodiment of the method of this invention will be described in detail by reference to FIG. 1.

The concentrated residue obtained by separating terephthalic acid from the oxidation reaction product withdrawn from the oxidation reactor and then recovering the reaction solvent from the mother liquor by, for example, distillation is fed from a pipe 1 into an extraction tank 2 equipped with a stirrer and, if desired, a heating device. Water as an extracting solvent is fed from a pipe 1, and a sulfur compound such as sodium sulfide is fed from a pipe 5. From a pipe 6, a gas containing molecular oxygen is introduced into the extracting tank, and the mixture is stirred for a predetermined period of time at a predetermined temperature. In this embodiment, the extracting treatment is performed in a single tank, but if desired, two tanks can be used, one tank for mixing the residue with water, and the other tank for treating the mixture of the residue and water with the molecular oxygen-containing gas and the sulfur compound.

The extracted mixture obtained after the stirring treatment is then cooled to a predetermined temperature in the tank 2, or else cooled after being transferred to a crystallization tank 3. The extracted mixture is fed to a solid-liquid separating device 8 through a pipe 7, and the extracted liquid phase separated here is recovered through a pipe 9. The separated residue, on the other hand, is withdrawn from a pipe 10, and sent to a treating step for the utilizing of organic substances such as the reaction intermediates. The extract containing the extracted catalyst is sent to a precipitating tank 11 from the pipe 9. The precipitating tank contains a predetermined amount of an alkali metal or ammonium carbonate or an aqueous solution of an alkali metal or ammonium carbonate fed from a reservoir 12. The extract containing the extracted catalyst is mixed with the alkali metal or ammonium carbonate in the precipitating tank at a predetermined temperature while stirring the mixture with a stirrer provided in the precipitating tank. Thus, a precipitate of a carbonate of the heavy metal catalyst is formed. The contents of the tank 11 are then supplied to a solid-liquid separator 14 via a pipe 13 for a solid-liquid separation. The liquid alkali-dissolved phase is discharged from a pipe 15. The precipitate of the carbonate of the heavy metal catalyst remaining in the separator is thoroughly washed with water introduced from a pipe 16 to remove the water-soluble materials completely, after which the heavy metal catalyst is recovered from a pipe 17 as a high purity carbonate having good filterability and washability.

In order to use the carbonate of the heavy metal catalyst so recovered again as an oxidation reaction catalyst, the carbonate is fed into a receptacle 18 from the pipe 17, and dissolved in a lower aliphatic carboxylic acid solvent and/or hydrobromic acid fed from a pipe 19 to prepare a catalyst solution, which is then withdrawn from a pipe 20 and recycled as the catalyst.

The operation of this invention described above can be performed either continuously or in a batchwise manner.

The operating conditions which are suitably used in the method of this invention are described in detail below.

The amount of water added to the extracting tank as a solvent for extracting the oxidation catalyst present in the residue of the reaction mother liquor is that amount required to extract the oxidation catalyst contained in the residue. If the amount of water is too large, other unwanted substances are also dissolved in addition to the oxidation catalyst, and the impurities are carried into the recovered catalyst. Furthermore, the efficiency of the operation is reduced as a result of an increase in the amount of the mixture treated. If the amount of water is less than the required amount, the rate of recovery of the catalyst is reduced, and the residue does not have sufficient flowability, which in turn renders the extracting operation difficult. Generally, the amount of water is about 0.5 to 6 times by weight, preferably 1 to 3 times, the weight of the residue.

At least one sulfur compound such as hydrogen sulfide, sodium sulfide, sodium hydrosulfide, potassium hydrosulfide and ammonium hydrosulfide is used in order to separate the small amounts of heavy metal impurities such as lead, molybdenum, copper or nickel mixed in the residue of the mother liquor as a result of the corrosion of the reaction apparatus. The amount of the sulfur compound added is that amount required to precipitate the trace amounts of the heavy metal impurities such as lead, molybdenum, copper or nickel as their sulfides. If the sulfur compound is added in an amount greater than necessary, the heavy metal catalyst also precipitates as a sulfide together with the heavy metal impurities, and this causes a decrease in the rate of recovery of the catalyst metal. For example, when cobalt is used as the heavy metal catalyst, and the amount of the sulfur compound added is 1% by weight calculated as sulfur based on the total weight of cobalt in the treating solution, the loss of the cobalt is 1.5%. When the sulfur compound is added in an amount of 0.3% by weight of the total amount of cobalt, the loss of the cobalt is 0.5%. Thus, with this amount of the sulfur compound, the effect of the present invention can be sufficiently achieved. Accordingly, the amount of the sulfur compound suitably added is not more than 1%, preferably not more than 0.7%, more preferably not more than 0.3%, by weight, calculated as sulfur based on the weight of the catalyst metal. When the sulfur compound is added to the mixture to be extracted, it is preferred to add the sulfur compound after diluting the sulfur compound with an inert medium such as air or water in order to disperse it uniformly and as rapidly as possible in the treating mixture. For example, hydrogen sulfide can be diluted with air or water, and the other sulfur compounds, with water.

Most advantageously, air is used as the gas containing molecular oxygen to be blown into the mixture of the residue of the mother liquor and water. The amount of the molecular oxygen-containing gas can be greater than the amount of oxygen absorbed in the treating mixture, and can be such a volume that a flow-out of excess oxygen containing gas is detected while stirring thoroughly the extraction system.

The higher the operating pressure, that is the partial pressure of oxygen, the shorter is the time required to remove the impurities in accordance with this invention. However, hardly any difference in the effect of removing the impurities according to the changes in the partial pressure of oxygen are observed. In view of the pressure resistance of the receptacle, a preferred operating pressure ranges from about normal atmospheric pressure to 10 $Kg/cm^2G$.

The extracting temperature is preferably from about room temperature (e.g., 20° – 30°C) to 100°C in view of the rate of recovery of the catalyst and the ease of operation. No appreciable increase in the rate of recovery of the catalyst and in the purity of the catalyst recovered is observed when the temperature is outside the above-specified range.

The treating time for the extraction differs according to the partial pressure of oxygen or the properties of the residue of the mother liquor, but usually, a suitable treating time is at least 20 minutes up to about 3 hours.

The extract obtained in the above treatment is subjected to solid-liquid separation using a conventional separator such as a filtering device. The temperature for the solid-liquid separation should be as low as possible in order to prevent the extract from becoming contaminated with impurities, and preferably is not higher than about 50°C, e.g., from about 0°C to about 50°C. The extraction residue separated is washed with water in order to increase the rate of recovery of the catalyst, and the wash liquid could be more effectively used as a solvent for the next cycle of extraction.

The solution containing the extracted catalyst which is free from the heavy metal impurities and most of the organic impurities usually contains about 0.1 to 10% by weight (as the metal) of the heavy metal catalyst such as cobalt or manganese. In order to recover the heavy metal catalyst as a highly pure carbonate, the extract is added to an alkali metal or ammonium carbonate or an aqueous alkali metal or ammonium carbonate solution. Examples of alkali metal or ammonium carbonates which can be used are sodium carbonate, sodium bicarbonate, potassium carbonate, potassium bicarbonate, and ammonium carbonate. The use of sodium carbonate is economically advantageous and thus preferred. The carbonate compound can be used in the form of either a solid or an aqueous solution. Preferably, an aqueous solution of from about 10 to 30% by weight is used. The carbonate compound must be added in an amount sufficient to increase the pH of the extract at least to a certain value. When sodium carbonate or potassium carbonate is used, the amount should be adjusted so that the pH of the extract becomes at least about 8.5, preferably 9.0 to 10.0. When potassium bicarbonate, sodium bicarbonate or ammonium carbonate is used, the amount should be adjusted so that the pH of the extract becomes at least about 7.5, preferably 8.0 to 9.0. By adjusting the pH of the extract as specified above, the remaining organic impurities are completely dissolved in the extract, and the heavy metal catalyst is separated as a carbonate precipitate of high purity. Thus, the trace amounts of the organic impurities that cannot be completely removed in the preceding extracting step can be separated without coprecipitation with the catalyst metal carbonate. If the amount of the alkali metal or ammonium carbonate is insufficient and the pH of the extract does not reach the desired value, organic impurities contaminate the precipitate of the carbonate of the heavy metal catalyst. It is not clear why this is so, but while not desiring to be bound it is presumed that the catalyst heavy metal is separated as if in the form of a complex salt of the organic impurities, in addition to being separated as the catalyst heavy metal carbonate. The higher the pH of the extract, the higher is the purity of the carbonate of the catalyst heavy metal, but on the other hand, the amount of the alkali metal or ammonium carbonate which must be used increases to an economic disadvantage. The amount of the alkali metal or ammonium carbonate is therefore determined by taking these factors into consideration.

When the precipitate of the carbonate of the heavy metal catalyst is formed by adding the catalyst extract to the alkali metal or ammonium carbonate, the temperature of the solution during the formation of the precipitate also affects the filterability and washability of the resulting precipitate. Therefore, it is necessary to adjust the temperature to about 26° to 70°C. If the temperature is lower than about 26°C, or higher than about 70°C, a precipitate of good filterability cannot be obtained.

Figure 2:
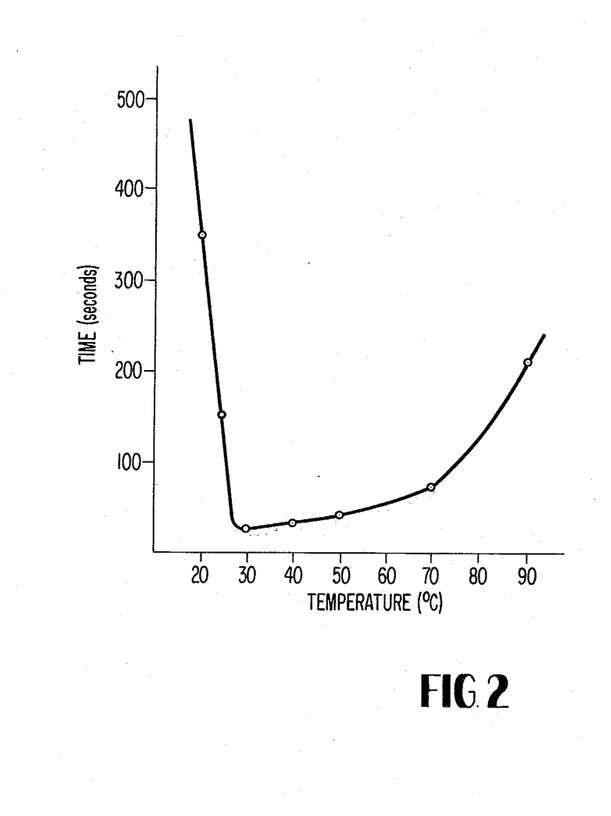
FIG. 2 is a graphical representation showing the relation between the temperature (°C) at which a heavy metal carbonate precipitate is formed, and the time (seconds) required to filter and wash the resulting precipitate.

FIG. 2 shows the relation between the temperature at which the precipitate of the carbonate of the heavy metal catalyst is formed, and the time required to separate the precipitate from the precipitate-containing solution by filtration and to wash the precipitate with water in the filter. As is clear from this graphical representation, the temperature for the formation of the precipitate should be maintained in the range of about 26° to 70°C, preferably 30° to 50°C.

The rate of formation of the precipitate, that is the rate of adding the extract, does not affect the filterability of the resulting precipitate as greatly, but the time required for adding the extract until the pH of the precipitate-containing solution reaches the desired value is suitably about 10 to 120 minutes. Even when the time is longer than the specified upper limit, no appreciable improvement in the filterability of the precipitate is observed. It is preferred that the formation of the precipitate be performed by agitating the precipitate-containing solution using a stirrer.

The precipitate-containing solution which contains the resulting precipitate having good filterability is then fed to a solid-liquid separating step in order to separate and recover the carbonate precipitate. The precipitate-containing solution can be fed directly to a filter device or centrifugal separator, etc., but if the precipitate-containing solution is diluted with a suitable amount of water and then subjected to a liquid-solid separating step, the carbonate precipitate in the precipitate-containing solution can be recovered without adsorption thereon of impurities such as the alkali metal due to the post-precipitation phenomenon. Thus, the dilution of the precipitate-containing solution prior to the solid-liquid separation is more preferred. The dilution of the precipitate-containing solution with water is especially effective when the precipitate-containing solution is allowed to stand for prolonged periods of time before being subjected to a solid-liquid separation after the formation of the precipitate. It is desirable to use as much diluting water as possible because the adsorption of the impurities can be inhibited to a greater extent. However, if the amount of water added is too great, the concentration of the carbonate precipitate in the solution decreases, and it becomes necessary to increase the filtration area in order to filter a fixed amount of the carbonate precipitate. Accordingly, a suitable amount of the water for dilution is at least about 0.5 times, preferably 0.5 to 2.0 times, by weight the total weight of the precipitate-containing solution.

Figure 3:
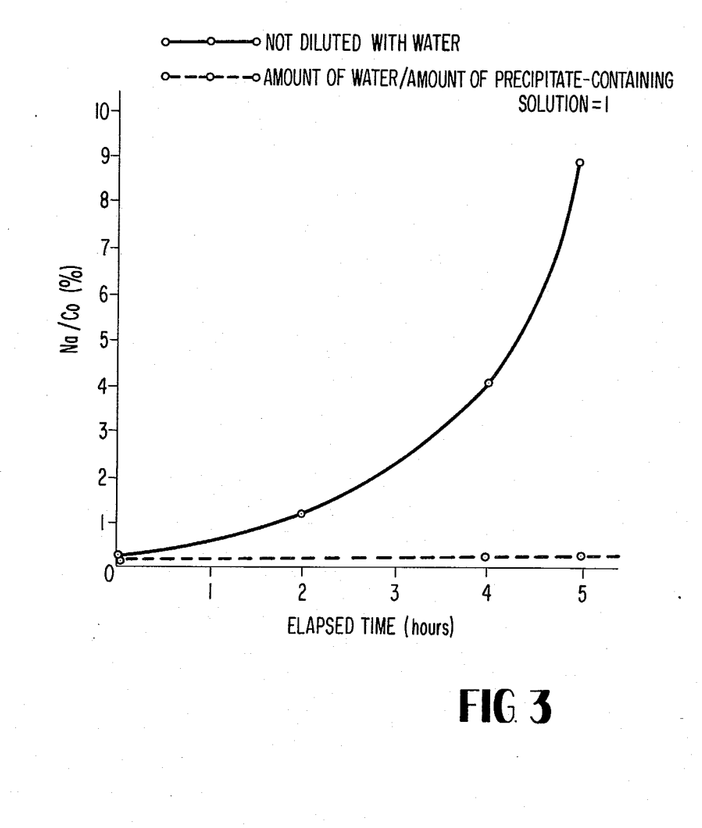
FIG. 3 is a graphical representation showing the relation between the elapsed time (hours) and the content (weight % based on the cobalt) of sodium in the resulting cobalt carbonate in the case of diluting the precipitate-containing solution with an equal amount of water after the formation of the precipitate, and where it is not diluted with water.

FIG. 3 shows the relation between the amount of sodium adsorbed on the recovered cobalt carbonate after a lapse of a certain period of time, and the time during which the precipitate-containing solution is allowed to stand, i.e. in situations wherein the precipitate-containing solution is allowed to stand as it is without diluting the precipitate-containing solution with water after the formation of the precipitate, and in situations wherein the solution is allowed to stand as it is after diluting the precipitate-containing solution with an equal weight of water. It can be seen from FIG. 3 that when the precipitate-containing solution is diluted with water after the formation of the precipitate, hardly any adsorption of impurities occurs even when the precipitate-containing solution is allowed to stand for long periods of time.

The solution containing the carbonate precipitate is fed to a filter device or a centrifugal separator either as it is or after diluting with water as described above, and subjected to a solid-liquid separation. The precipitate separated is washed with water in the filter device or centrifugal separator in order to remove water soluble impurities such as the alkali metal or ammonium carbonate adhering to the carbonate precipitate. The amount of water used for washing is suitably at least 10 times, preferably 50 to 200 times, by weight, the weight of the carbonate precipitate of the heavy metal catalyst.

According to the method of this invention described above in detail, the heavy metal oxidation catalyst such as cobalt or manganese can be recovered at a rate as high as more than about 95% as a carbonate precipitate having high purity and good filterability and washability from the residue obtained in the separation of terephthalic acid and the solvent from the liquid phase oxidation reaction product of alkylbenzenes. Moreover, the heavy metal catalyst recovered is not contaminated with organic impurities, heavy metal impurities such as iron, chromium, lead, molybdenum, tungsten, copper or nickel present in the residue as a result of the corrosion of the equipment, and other impurities such as alkali metals which are detrimental to the oxidation reaction used in producing terephthalic acid.

The resulting highly pure carbonate of the heavy metal catalyst is dissolved in a lower aliphatic carboxylic acid such as acetic acid as a reaction solvent, and if desired a bromine compound is further added to adjust the composition of the catalyst to the desired concentration. Then, the catalyst can be recycled to the liquid phase oxidation reaction.

The following Examples illustrate the present invention in greater detail. Unless otherwise indicated, all parts, percents, ratios and the like are by weight.

EXAMPLE 1 p-Xylene was oxidized with air in the liquid phase in the presence of acetic acid as a solvent using cobalt bromide and manganese acetate (5.0% by weight of manganese metal based on the cobalt metal) as a catalyst. The resulting terephthalic acid was separated from the reaction product, and the reaction mother liquor was distilled to recover the acetic acid. The distillation residue contained the heavy metal catalysts and heavy metal impurities in the amounts indicated in the following table.

|  | Co (%) | Mn (%) | Heavy Metal Fe (%) | Cr (%) | Mo (ppm) | Pb (ppm) | Cu (ppm) |
|---|---|---|---|---|---|---|---|
| Content | 5.0 | 0.21 | 0.34 | 0.08 | 6.1 | 4.4 | 13.0 |

A reaction tank equipped with a stirrer and a heating device was charged with 700 parts of the resulting residue and 1000 parts of water, and the mixture was heated to 70°C. Then, 30 parts of a 0.5% aqueous solution of sodium hydrosulfide was charged in the tank, and air was introduced into the mixture to a pressure of 1.5 Kg/cm²G. The mixture was then stirred for one hour. During this time, air was discharged at a rate of 18 N liters/min per 100 Kg of the contents being treated. The contents were then withdrawn and fed into a crystallization tank, and cooled to 30°C, followed by subjecting to a solid-liquid separation using a centrifugal separator to obtain 900 parts of the extract and 800 parts of the filtration residue. The filtration residue was washed with 800 parts of water, and the wash liquid was combined with the extract to obtain 1700 parts of the catalyst extract. 500 parts of the catalyst extract were gradually added into 400 parts of a 15% aqueous solution of sodium carbonate placed in a tank over the course of about 1 hour while maintaining the temperature of the solution at 30°C, thereby to form a precipitate of cobalt carbonate and manganese carbonate. The precipitate-containing solution had a pH of 9.1. After standing for about 4 hours, 900 parts of the precipitate-containing solution was filtered under a reduced pressure at 400 mmHg using a Buchner funnel having a diameter of 23 cm (filtering area 415 cm²), and then washed with 900 parts of water in order to remove the precipitation mother liquor adhering to the precipitate. 62 parts of a cake was obtained. The cake contained the heavy metals in the amounts shown in the following table. From the result obtained, the rate of recovery of cobalt from the residue was found to be 97%.

|  | Co (%) | Mn (%) | Fe (%) | Heavy Metals Cr (%) | Mo (ppm) | Pb (ppm) | Cu (ppm) |
|---|---|---|---|---|---|---|---|
| Content | 16.1 | 0.66 | 0.02 | 0.002 | less than 3 | less than 3 | less than 3 |

The time required to filter the precipitate from the precipitate-containing solution and to wash the precipitate, and the amount (percent by weight based on the metallic cobalt) of sodium remaining in the recovered cake are shown in Table 1.

EXAMPLE 2

Example 1 was repeated except that the temperature of the liquid at the time of forming the precipitate by adding the catalyst extract to the aqueous solution of sodium carbonate was changed to 50°C. The time required for the filtration and washing of the precipitate and the amount of the remaining sodium are shown in Table 1.

EXAMPLE 3

Example 1 was repeated except that the temperature of the liquid at the time of forming the precipitate by adding the catalyst extract to the aqueous solution of sodium carbonate was changed to 70°C. The results obtained are shown in Table 1.

EXAMPLE 4

Example 1 was repeated except that the precipitate resulting from the suction filtration of the precipitate-containing solution was washed with 1800 parts of water. The results obtained are shown in Table 1.

EXAMPLE 5

500 parts of the catalyst extract obtained using the same method as in Example 1 was added to 400 parts of a 15% by weight aqueous solution of sodium carbonate. 900 parts of the resulting precipitate-containing solution was diluted with 450 parts (0.5 times the weight of the precipitate-containing solution) of water, and allowed to stand for 4 hours. Then, it was filtered under a reduced pressure, and the precipitate was washed with 450 parts of water to form a cake. The results obtained are shown in Table 1. The amount of the residual sodium was reduced remarkably because the precipitate-containing solution was diluted with water prior to filtration.

EXAMPLE 6

Example 5 was repeated except that 900 parts of the precipitate-containing solution was diluted with 900 parts of water. The results obtained are shown in Table 1.

Table 1

| Example | Temperature for Precipitate Formation (°C) | Amount of Water to Dilute the Precipitate-Containing Solution (water/solution) | Amount of Washing Water (parts) | Time Required for Filtration and Washing (seconds) | Amount of Sodium Remaining in the Cake (wt.%/Co) |
|---|---|---|---|---|---|
| 1 | 30 | 0 | 900 | 25 | 4.0 |
| 2 | 50 | 0 | 900 | 40 | 4.1 |
| 3 | 70 | 0 | 900 | 70 | 4.5 |
| 4 | 30 | 0 | 1800 | 40 | 3.5 |
| 5 | 30 | 0.5 | 450 | 25 | 0.5 |

Table 1-continued

| Example | Temperature for Precipitate Formation (°C) | Amount of Water to Dilute the Precipitate-Containing Solution (water/solution) | Amount of Washing Water (parts) | Time Required for Filtration and Washing (seconds) | Amount of Sodium Remaining in the Cake (wt.%/Co) |
|---|---|---|---|---|---|
| 6 | 30 | 1.0 | 450 | 30 | 0.2 |

COMPARATIVE EXAMPLE 1

Example 1 was repeated except that in the formation of the precipitate by mixing the catalyst extract with sodium carbonate, 400 parts of the 15% by weight aqueous solution of sodium carbonate was added to 500 parts of the catalyst extract contrary to the procedures of Example 1. The time required to filter the precipitate-containing solution and wash the precipitate was 400 seconds. This means that the precipitate had a much poorer filterability and washability than the precipitate obtained in Example 1.

COMPARATIVE EXAMPLE 2

Example 1 was repeated except that in the formation of the precipitate by mixing the catalyst extract with the aqueous solution of sodium carbonate, 400 parts of the 15% by weight aqueous solution of sodium carbonate was added to 500 parts of the catalyst extract contrary to the method of Example 1, and during this time, the temperature of the liquid was maintained at 90°C. The time required to filter the precipitate-containing solution and wash the precipitate was 200 seconds. This means that the precipitate obtained had poor filterability and washability.

COMPARATIVE EXAMPLE 3

Example 1 was repeated except that the temperature of the liquid at the time of forming the precipitate by adding the catalyst extract to the aqueous solution of sodium carbonate was maintained at 20°C. The time required to filter the precipitate-containing solution and wash the precipitate was 350 seconds. The precipitate had poor filterability and washability because the temperature of the liquid was outside the range specified in the present invention.

COMPARATIVE EXAMPLE 4

Example 1 was repeated except that the temperature of the liquid at the time of forming the precipitate by adding the catalyst extract to the aqueous solution of sodium carbonate was maintained at 90°C (which is outside the range specified in the present invention). The time required to filter the precipitate-containing solution and wash the precipitate was 210 seconds. This means that the resulting precipitate had poor filterability and washability.

While the invention has been described in detail and with reference to specific embodiments thereof, it will be apparent to one skilled in the art that various changes and modifications can be made therein without departing from the spirit and scope thereof.

What is claimed is:

1. A method for recovering a heavy metal oxidation catalyst comprising a metal selected from cobalt and manganese from the residue of the reaction mother liquor containing the heavy metal oxidation catalyst, organic impurities and a small amount of heavy metal impurities, said residue being obtained by removing a solvent selected from a lower aliphatic monocarboxylic acid from the reaction mother liquor remaining after recovering terephthalic acid from the oxidation reaction product obtained in the process for producing terephthalic acid by subjecting an alkylbenzene to a liquid-phase oxidation with oxygen or an oxygen-containing gas in the presence of the heavy metal oxidation catalyst using said solvent, which comprises:

A. stirring an aqueous dispersion of said residue in the presence of a sulfur compound selected from the group consisting of hydrogen sulfide, sodium sulfide, sodium hydrosulfide, potassium hydrosulfide and ammonium hydrosulfide while contacting a gas containing molecular oxygen with said dispersion wherein the amount of the sulfur compound is not more than about 1% by weight calculated as sulfur based on the weight of the heavy metal component of the catalyst and the amount of water in the aqueous dispersion is about 0.5 to 6 times of the weight of the residue, thereby to extract said heavy metal oxidation catalyst into said aqueous phase, and to precipitate organic impurities and heavy metal impurities, B. subjecting said aqueous dispersion to a solid-liquid separation at a temperature of not more than about 50°C to separate the solid organic impurities and heavy metal impurities and obtain an aqueous solution containing the oxidation catalyst, C. adding the aqueous solution containing the oxidation catalyst to an alkali metal or ammonium carbonate or an aqueous solution of an alkali metal or ammonium carbonate while maintaining the temperature of the system at about 26°C to 70°C, to form a solution containing a precipitate of a carbonate of the heavy metal catalyst, and D. subjecting the solution containing the precipitate of the carbonate of the heavy metal catalyst to a solid-liquid separation to recover the heavy metal catalyst as a carbonate precipitate.

2. The method of claim 1, wherein the catalyst comprises cobalt, manganese and bromine as catalyst components.

3. The method of claim 1, wherein the amount of the sulfur compound is not more than about 0.3% by weight calculated as sulfur based on the weight of the heavy metal component of the catalyst.

4. The method of claim 1, wherein said sulfur compound comprises hydrogen sulfide diluted with air or water, and the other sulfur compounds diluted with water.

5. The method of claim 1, wherein said gas containing molecular oxygen is air.

6. The method of claim 1, wherein said alkali metal or ammonium carbonate is selected from the group consisting of sodium carbonate, sodium bicarbonate, potassium carbonate, potassium bicarbonate and ammonium carbonate.

7. The method of claim 6, wherein said alkali metal carbonate is sodium carbonate.

8. The method of claim 6, wherein in step (C) said alkali metal carbonate is sodium carbonate or potassium carbonate and the pH of said precipitate-containing solution is adjusted to at least about 8.5.

9. The method of claim 8, wherein in step (C) said alkali metal or ammonium carbonate is sodium carbonate or potassium carbonate and the pH of said precipitate-containing solution is adjusted to 9.0 to 10.0.

10. The method of claim 6, wherein in step (C) said alkali metal or ammonium carbonate is sodium bicarbonate, potassium bicarbonate or ammonium carbonate and the pH of said precipitate-containing solution is adjusted to at least about 7.5.

11. The method of claim 10, wherein in step (C) said alkali metal or ammonium carbonate is sodium bicarbonate, potassium bicarbonate or ammonium carbonate and the pH of said precipitate-containing solution is adjusted to 8.0 to 9.0.

12. The method of claim 1, wherein in step (C) the temperature of the precipitate-containing solution at the time of forming the precipitate is maintained at about 30° to 50°C.

13. The method of claim 1, including diluting the precipitate-containing solution obtained in step (C) with water prior to subjecting said solution to said solid-liquid separation.

14. The method of claim 13, wherein the amount of said diluting water is at least about 0.5 times by weight the total weight of said precipitate-containing solution.

15. The method of claim 13, wherein the amount of said diluting water is about 0.5 to 2.0 times by weight the total weight of said precipitate-containing solution.

16. The method of claim 1, wherein in step (A) the amount of water in the aqueous dispersion is about 1 to 3 times the weight of the residue.

17. The method of claim 1, wherein the stirring of step (A) is carried out under a pressure of from about normal atmospheric pressure to 10 Kg/cm$^2$G.

18. The method of claim 1, wherein the time of the stirring in step (A) is at least 20 minutes up to about 3 hours.

19. The method of claim 1, wherein the stirring of step (A) is carried out at a temperature within the range of about room temperature to 100°C.

20. The method of claim 1, wherein the step (C) the concentration of said aqueous solution of an alkali metal or ammonium carbonate is about 10 to 30% by weight.

21. The method of claim 1, wherein the solvent is acetic acid.

* * * * *